(12) United States Patent
Li et al.

(10) Patent No.: US 11,074,800 B2
(45) Date of Patent: Jul. 27, 2021

(54) FALL DETECTION METHOD AND APPARATUS

(71) Applicant: Fujitsu Limited, Kawasaki (JP)

(72) Inventors: Hongchun Li, Beijing (CN); Genming Ding, Beijing (CN); Qian Zhao, Beijing (CN); Lili Xie, Beijing (CN); Jun Tian, Beijing (CN)

(73) Assignee: FUJITSU LIMITED, Kawasaki (JP)

( * ) Notice: Subject to any disclaimer, the term of this patent is extended or adjusted under 35 U.S.C. 154(b) by 3 days.

(21) Appl. No.: 16/665,518

(22) Filed: Oct. 28, 2019

(65) Prior Publication Data

US 2020/0143656 A1 May 7, 2020

(30) Foreign Application Priority Data

Nov. 2, 2018 (CN) .......................... 201811301466.X

(51) Int. Cl.
*G08B 21/04* (2006.01)
*G01S 7/41* (2006.01)
*G01S 13/89* (2006.01)

(52) U.S. Cl.
CPC .......... *G08B 21/0446* (2013.01); *G01S 7/411* (2013.01); *G01S 13/89* (2013.01); *A61B 2562/046* (2013.01)

(58) Field of Classification Search
None
See application file for complete search history.

(56) References Cited

U.S. PATENT DOCUMENTS

| 5,361,070 A | 11/1994 | McEwan | |
|---|---|---|---|
| 7,567,200 B1 * | 7/2009 | Osterweil | A61B 5/1117 342/28 |
| 7,593,692 B2 * | 9/2009 | Hansen | G01S 7/021 455/226.1 |
| 7,612,681 B2 * | 11/2009 | Azzaro | G16H 50/30 340/573.4 |

(Continued)

FOREIGN PATENT DOCUMENTS

| CN | 105814450 | 7/2016 |
|---|---|---|
| CN | 106530619 | 3/2017 |

(Continued)

OTHER PUBLICATIONS

Partial European Search Report dated Mar. 10, 2020 in European Patent Application No. 19205317.1.

(Continued)

*Primary Examiner* — Muhammad Adnan
(74) *Attorney, Agent, or Firm* — Staas & Halsey LLP

(57) ABSTRACT

Embodiments of this disclosure provide a fall detection method and apparatus. The apparatus acquires information of radar reflection points belonging to a detected object in a predetermined number of consecutive frames, information on a radar reflection point including at least two of information on a position, information on a radial velocity and information on reflection signal strength, of the reflection point; determines whether the detected object has fallen according to a relationship between time and the information on radar reflection points in the predetermined number of consecutive frames.

13 Claims, 7 Drawing Sheets

(56) References Cited

U.S. PATENT DOCUMENTS

| | | | | |
|---|---|---|---|---|
| 7,887,489 B2* | 2/2011 | Lee | A61B 5/0507 | |
| | | | 600/484 | |
| 7,916,066 B1* | 3/2011 | Osterweil | A61B 5/1117 | |
| | | | 342/28 | |
| 8,217,795 B2* | 7/2012 | Carlton-Foss | A61B 5/0024 | |
| | | | 340/573.1 | |
| 8,427,324 B2* | 4/2013 | Cuddihy | G08B 21/0476 | |
| | | | 340/573.1 | |
| 2006/0001545 A1 | 1/2006 | Wolf | | |
| 2008/0154524 A1* | 6/2008 | Shirley | G01B 9/02096 | |
| | | | 702/66 | |
| 2013/0002434 A1* | 1/2013 | Cuddihy | G08B 21/043 | |
| | | | 340/573.7 | |
| 2014/0362213 A1 | 12/2014 | Tseng | | |
| 2016/0379462 A1* | 12/2016 | Zack | G01S 7/411 | |
| | | | 340/539.12 | |
| 2017/0042432 A1 | 2/2017 | Adib et al. | | |
| 2018/0102035 A1 | 4/2018 | Trishaun | | |
| 2018/0192919 A1 | 7/2018 | Nakayama et al. | | |
| 2018/0292523 A1 | 10/2018 | Orenstein et al. | | |
| 2020/0166610 A1* | 5/2020 | Lin | G01S 7/415 | |
| 2020/0166611 A1* | 5/2020 | Lin | G01S 13/42 | |
| 2020/0191913 A1* | 6/2020 | Zhang | G01S 7/006 | |

FOREIGN PATENT DOCUMENTS

| | | |
|---|---|---|
| CN | 107749143 | 3/2018 |
| CN | 108279413 | 7/2018 |
| WO | 2016/155789 | 10/2016 |

OTHER PUBLICATIONS

Extended European Search Report dated Jun. 8, 2020 in European Patent Application No. 19205317.1.

* cited by examiner

401 Calculating average reflection point information of a plurality of radar reflection points belonging to the detected object in each frame

402 Calculating a first feature value and a second feature value of the average reflection point information in the first predetermined number of consecutive frames

403 Determining whether the detected object falls according to the first feature value and the second feature value

Fig. 4

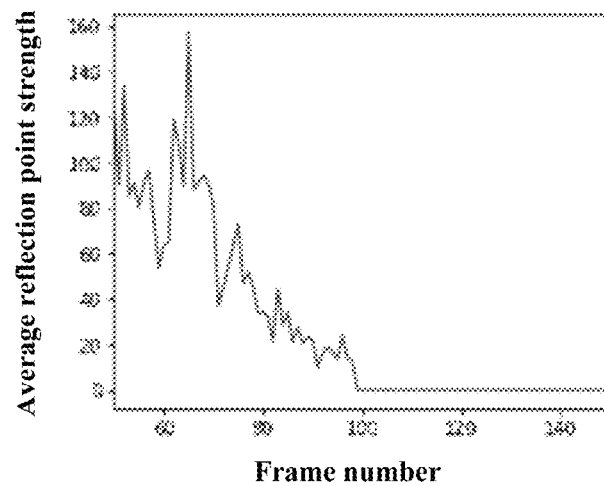

Fig. 5

FALL DETECTION METHOD AND APPARATUS

CROSS-REFERENCE TO RELATED APPLICATIONS

This application is based on and hereby claims priority to Chinese Application No. 201811301466.X, filed Nov. 2, 2018, in the State Intellectual Property Office of China, the disclosure of which is incorporated herein by reference.

TECHNICAL FIELD

This disclosure relates to the field of information technologies, and in particular to a fall detection method and apparatus.

BACKGROUND

Fall often occurs in people's daily lives. Fall may cause different degrees of damages to bodies due to different physical conditions of people. According to a report from the World Health Organization, the number of times of fatal falls in a year is 646,000, those are causes of the second largest unintentional injury death after road traffic injuries. Timely detection of falls and rescue of injured people can prevent injuries from being aggravated and mitigate fatal risks. Therefore, fall detection is important for creating a safe and livable living environment.

Currently, common fall detection methods include methods based on wearable devices and methods based on videos. A fall detection method based on a wearable device requires a user to wear a terminal equipment, and uses information from a sensor (such as an acceleration sensor, or the like) in the terminal equipment to detect whether the user falls. However, wearing a wearable device may possibly cause discomfort to the body and the user experience is poor. A fall detection method based on a video requires a camera to be installed in a monitoring area to detect if someone falls through image and video information. However, such a method may infringe people's privacy and cannot be applied to privacy-sensitive surveillance areas.

It should be noted that the above description of the background is merely provided for clear and complete explanation of this disclosure and for easy understanding by those skilled in the art. And it should not be understood that the above technical solution is known to those skilled in the art as it is described in the background of this disclosure.

SUMMARY

At present, in the relevant art, a fall detection method based on a microwave radar is proposed, in which the microwave radar may transmit a microwave signal to a detected object, and after the microwave signal is reflected by the detected object, the microwave radar may receive a reflected signal, obtain information on a height of the detected object according to the reflected signal, and perform fall detection according to the information on a height. For example, when the height is lower than a predetermined value, it indicates that the detected object falls.

However, it was found by the inventors that if the information on a height is taken into account only, error detection may be resulted in some scenarios (such as those where the detected object crouches down, or sits down, etc.).

Embodiments of this disclosure provide a fall detection method and apparatus, so as to solve the problems existing in the relevant art.

According to an embodiment the fall detection apparatus comprises a memory and a processor coupled to the memory and the processor configured to acquire information on radar reflection points belonging to a detected object in a first predetermined number of consecutive frames, information on a radar reflection point including at least two of information on a position, information on a radial velocity and information on reflection signal strength, of the reflection point; and determine whether the detected object falls according to a relationship between time and the information on radar reflection points in the first predetermined number of consecutive frames.

According to an embodiment includes a fall detection apparatus which comprises a memory and a processor coupled to the memory and the processor configured to acquire information on radar reflection points belonging to a detected object in a first predetermined number of consecutive frames, information on a reflection point including at least two of information on a position, information on a radial velocity and information on reflection signal strength, of the reflection point, and calculate feature values according to the information on radar reflection points in the first predetermined number of consecutive frames, the feature values including at least two of the following features: a feature related to the number of reflection points of a radar reflection plane or a feature related to reflection signal strength of a radar reflection plane, a feature related to a height of a radar transmission point, a feature related to a velocity of a radar transmission point, and a feature related to a reflection point trajectory of a radar reflection plane. The processor of the fall detection apparatus further determines whether the detected object falls according to the feature values.

According to an embodiment, a fall detection method comprises acquiring information on radar reflection points belonging to a detected object in a first predetermined number of consecutive frames, information on a radar reflection point including at least two of information on a position, information on a radial velocity and information on reflection signal strength, of the reflection point; and determining whether the detected object falls according to a relationship between time and the information on radar reflection points in the first predetermined number of consecutive frames.

According to an embodiment a fall detection method includes acquiring information on radar reflection points belonging to a detected object in a first predetermined number of consecutive frames, information on a reflection point including at least two of information on a position, information on a radial velocity and information on reflection signal strength, of the reflection point; calculating feature values according to the information on radar reflection points in the first predetermined number of consecutive frames, the feature values including at least two of the following features: a feature related to the number of reflection points of a radar reflection plane or a feature related to reflection signal strength of a radar reflection plane, a feature related to a height of a radar transmission point, a feature related to a velocity of a radar transmission point, and a feature related to a reflection point trajectory of a radar reflection plane; and determining whether the detected object falls according to the feature values.

One advantage of the embodiments of this disclosure exists in that whether the detected object has fallen is determined according to a relationship between time and at least two of information on a position, information on a radial velocity and information on reflection signal strength in the information on reflection points obtained by the microwave radar, in which a terminal equipment needs not to be worn by the user, and use experience is good, which is applicable to monitoring a private area, may perform fall detection according to information on multi-dimensional reflection points, with the precision being more higher, the rate of error report being lower, and the detection speed being faster.

With reference to the following description and drawings, the particular embodiments of this disclosure are disclosed in detail, and the principle of this disclosure and the manners of use are indicated. It should be understood that the scope of the embodiments of this disclosure is not limited thereto. The embodiments of this disclosure contain many alternations, modifications and equivalents within the spirits and scope of the terms of the appended claims.

Features that are described and/or illustrated with respect to one embodiment may be used in the same way or in a similar way in one or more other embodiments and/or in combination with or instead of the features of the other embodiments.

It should be emphasized that the term "comprise/include" when used in this specification is taken to specify the presence of stated features, integers, blocks or components but does not preclude the presence or addition of one or more other features, integers, blocks, components or groups thereof.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. To facilitate illustrating and describing some parts of the disclosure, corresponding portions of the drawings may be exaggerated or reduced in size. Elements and features depicted in one drawing or embodiment of the disclosure may be combined with elements and features depicted in one or more additional drawings or embodiments. Moreover, in the drawings, like reference numerals designate corresponding parts throughout the several views and may be used to designate like or similar parts in more than one embodiment.

In the drawings:

FIG. 4 is a flowchart of determining whether a detected object has fallen according to an embodiment;

FIG. 5 is a schematic diagram of variation of reflection point strength information along with time (frame number) in a fall process according to an embodiment;

DETAILED DESCRIPTION

These and further aspects and features of the present invention will be apparent with reference to the following description and attached drawings. These embodiments are illustrative only, and are not intended to limit this disclosure. For the principle of and embodiments of this disclosure to be easily understood by those skilled in the art, the embodiments of this disclosure shall be described by taking a reconstructed image in image compression processing as an example. However, it should be understood that the embodiments of this disclosure are not limited thereto, and reconstructed images based on other image processing are also covered by the scope of this disclosure.

The embodiments of this disclosure shall be described below with reference to the accompanying drawings.

Figure 1:
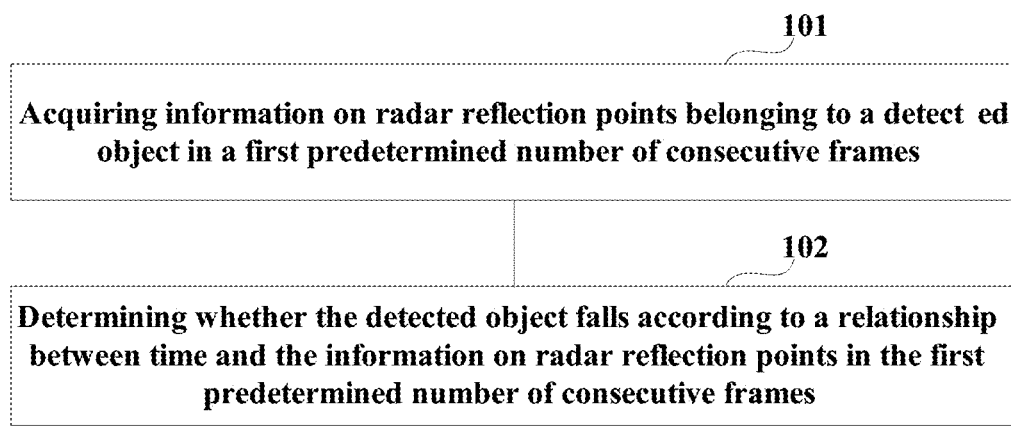
FIG. 1 is a flowchart of the fall detection method according to an embodiment.

FIG. 1 is a flowchart of a fall detection method. As shown in FIG. 1, the method includes:

Block (operation) 101: acquiring information on radar reflection points belonging to a detected object in a first predetermined number of consecutive frames, information on a radar reflection point including at least two of information on a position, information on a radial velocity and information on reflection signal strength, of the reflection point; and Block 102: determining whether the detected object falls according to a relationship between time and the information on radar reflection points in the first predetermined number of consecutive frames.

In an embodiment, a microwave signal, such as a frequency-modulated continuous wave (FMCW), may be transmitted to a detected object (a person) by a preset microwave radar, and a reflected signal, which is formed after the microwave signal is reflected by an obstacle in the environment and the detected object, is received by the microwave radar.

Figure 2:
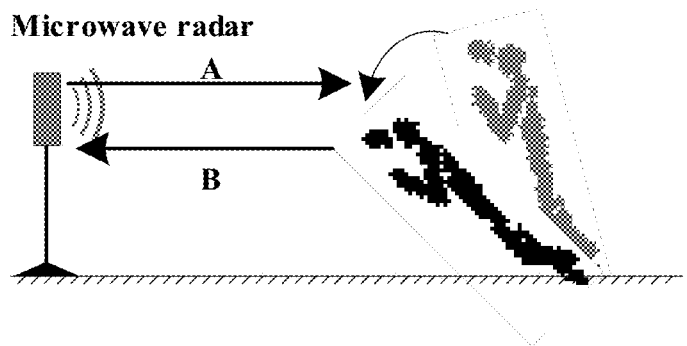
FIG. 2 is a schematic diagram of receiving and transmitting signals by the microwave radar according to an embodiment.

FIG. 2 is a schematic diagram of transmitting and receiving signals by the microwave radar. As shown in FIG. 2, the microwave radar transmits a microwave signal A and receives a reflected signal B after being reflected. When a multi-antenna technique is used, the microwave signal A may include different microwave signals transmitted by different transmitting antennas; and the reflected signal B changes in frequency and phase in comparison with the microwave signal A, and therefore, based on the microwave signal A and the reflected signal B, information on radar reflection points belonging to the detected object can be acquired. Measurement result obtained by the microwave radar for one time shall be taken as information on a frame of radar reflection points in the following description.

Figure 3:
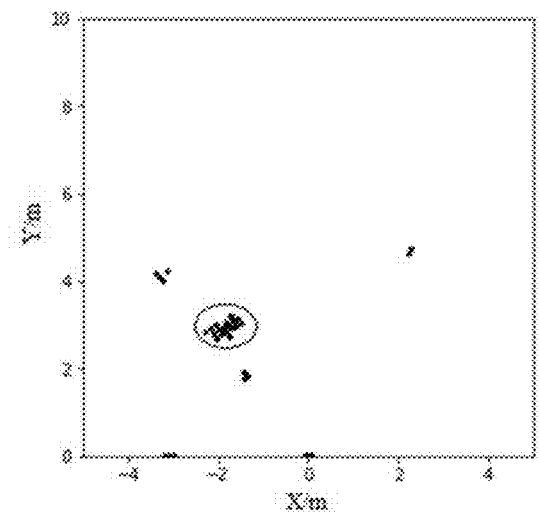
FIG. 3 is a schematic diagram of distribution of a frame of radar reflection points in an X-Y plane according to an embodiment.

FIG. 3 is a schematic diagram of distribution of a frame of radar reflection points in an X-Y plane. As shown in FIG. 3, reflection points in a circle belongs to the radar reflection points of the detected object, and the other points are reflection points of other obstacles in the environment (hereinafter referred to as noise points). An existing tracking algorithm or an existing clustering algorithm (such as a density-based spatial clustering of applications with noise algorithm (DBSCAN algorithm)) may be used to distinguish whether radar reflection points belong to the reflection points of the detected object or the noise points. In block 102, the fall detection is performed according to the information on radar reflection points within the first predetermined number (N) of consecutive frames belonging to the detected object.

In an embodiment, the microwave radar may include transmitting antennas, receiving antennas, a circuit, and a memory, etc. The numbers of the transmitting antennas and the receiving antennas may be more than one. The transmitting antennas may be used to transmit microwave signals, and the receiving antennas may be used to receive reflected signals. The memory may store information utilized by various processing of operations of the microwave radar. The circuit may be configured to include a processor executing control programs, such as acquiring information on a reflection point based on the transmitted microwave signal and the reflected signal.

The information on a reflection point includes at least two of information on a position, information v on a radial velocity and information p on reflection signal strength, of the reflection point. The information on the position of the reflection point including at least one of information r on a distance between the reflection point and a radar and information on three-dimensional coordinates (x, y, z) of the reflection point. In particular, information p on strength may be obtained according to the received reflected signal, and the information on three-dimensional coordinates (x, y, z) of the reflection point may be determined according to an angle of departure of the transmitting antennas and an angle of arrival of the receiving antennas. Furthermore, there exists a frequency difference between the reflected signal and the transmitted microwave signal, the frequency difference is proportional to a distance r between the microwave radar and the detected object.

The microwave signal and the reflected signal are processed to obtain a baseband signal; when the detected object has a radial velocity v with respect to the microwave radar (a velocity towards the microwave radar, a Doppler velocity), a frequency of the baseband signal is changing. Information on the velocity v and the distance r is included in the changing frequency, and the information on the velocity v and the distance r may be obtained by performing two-dimensional Fourier transform (2D-FFT).

Reference may be made to the relevant art for a structure of the microwave radar, and reference may also be made to the relevant art for a calculation method for acquiring the above-mentioned reflection point information, with details being not going to be described herein any further. It should be noted that this disclosure is not limited to using the circuit inside the microwave radar to obtain the information on the reflection point, and alternatively, the microwave signal and the reflection signal may be transmitted to other devices to obtain the information on the reflection point.

In an embodiment, as shown in FIG. 2, in the fall process, the detected object is changed from the upright state into a lying state in a short period of time. In this process, a reflection surface of the detected object towards the microwave signal gradually reduces, the height is lowered, the radial velocity is increased, and the trajectory on the X-Y plane presents a shape like a straight line. Therefore, the information on radar reflection points may be used to calculate at least two of the following feature values: a feature related to the number of reflection points of the radar reflection surface or a feature related to the reflected signal strength, a feature related to a height of a radar transmission point, a feature related to a velocity of the radar transmission point, and a feature related to a reflection point trajectory of the radar reflection surface; and the fall detection is performed according to a combination of at least two features.

In block 102, whether the detected object falls or not may be determined according to the relationship between the information on radar reflection points in the first predetermined number of consecutive frames and time.

FIG. 4 is a schematic diagram of an embodiment of 102. In an embodiment, the relationship between the radar reflection points and the time may be denoted by a first feature value and a second feature value. As shown in FIG. 4, the method includes:

Block 401: calculating average reflection point information of a plurality of radar reflection points belonging to the detected object in each frame;

Block 402: calculating a first feature value and a second feature value of the average reflection point information in the first predetermined number of consecutive frames; and Block 403: determining whether the detected object falls according to the first feature value and the second feature value.

In block 401, the information on reflection point includes at least two of information on a position, information v on a radial velocity and information p on reflection signal strength, of the reflection point, the information on the position of the reflection point including at least one of information r on a distance between the reflection point and a radar and information on three-dimensional coordinates (x, y, z) of the reflection point. In block 401, the number of radar reflection points belonging to the detected object of each of N frames is $n_1, n_2, \ldots n_N$. An average value of the above-mentioned information on reflection point to which each reflection point of each frame corresponds is calculated to obtain average reflection point information of each frame.

In block 402, a first feature value and a second feature value of average reflection point information of the N frames are calculated to reflect the relationship between radar reflection point and time, the first feature value denoting a parameter of the average reflection point information related to time variation, and the second feature value denoting a statistical value of average reflection point information of a second predetermined number of consecutive frames located behind in the first predetermined number of consecutive frames, and/or denoting a difference between a statistical value of average reflection point information of a third predetermined number of consecutive frames located front in the first predetermined number of consecutive frames and a statistical value of average reflection point information of a second predetermined number of consecutive frames located behind in the first predetermined number of consecutive frames.

For example, when the reflection point information is the information z on height in the spatial three-dimensional coordinate information of the reflection point, or the information p on reflected signal strength, or the information v on a radial velocity, average reflection point information to which each frame corresponds is $\bar{z}$, $\bar{p}$, $\bar{v}$. The first feature value denotes the parameter of the average reflection point information related to time variation, the parameter being, for example, a rate of variation of linear fitting (a slope) between the average reflection information and time, and/or a coefficient of correlation between the average reflection information and time, and the second feature value being an average value of the average reflection point information of the second predetermined number of consecutive frames located behind.

For example, when the reflection point information is information on horizontal and vertical coordinates (x, y) of a horizontal plane in the information on spatial three-dimensional coordinates of the reflection point, average reflection point information to which each frame corresponds is $(\bar{x}, \bar{y})$, the first feature value is a linear fitting error between average reflection point information $\bar{x}$ of the horizontal coordinate and average reflection point information $\bar{y}$ of the vertical coordinate, and/or a coefficient of correlation between average reflection point information $\bar{x}$ of the horizontal coordinate and average reflection point information $\bar{y}$ of the vertical coordinate, and the second feature value is a distance between a coordinate trajectory center of a horizontal plane of the third predetermined number of consecutive frames located front and a coordinate trajectory center of a horizontal plane of the second predetermined number of consecutive frames located behind.

How to calculate the first feature value and the second feature value for the above-described reflection point information shall be described below.

1) For Reflected Signal Strength Information p.

FIG. 5 is a schematic diagram of variation of the average reflection point information $\bar{p}$ along with time (frame number) in a fall process. As shown in FIG. 5, when the fall occurs, due to gradual decrease of the reflection surface of the detected object, the average reflection point information $\bar{p}$ is gradually reduced, but is not increased nor decreased extremely quickly. The first feature value may be the rate of variation (slope) Stp of linear fitting between the average reflection information $\bar{p}$ and time (N frames) and/or a coefficient of correlation Rtp between the average reflection information $\bar{p}$ and time (N frames). Reference may be made to the relevant art for a method for calculating the slope of linear fitting and the coefficient of correlation. A variation tendency (gradually decreasing or increasing, or extremely quickly decreasing, etc.) of the average reflection information $\bar{p}$ may be reflected according to the slope Stp, and a magnitude of the linear correlation between the average reflection information $\bar{p}$ and time may be reflected according to the coefficient of correlation Rtp, a range of value of which being [−1, 1] (for example, the coefficient of correlation in the fall process should be of a value close to −1, in other words, if a difference between a coefficient of correlation obtained through calculation and −1 is less than or equal to a specified threshold, it is possible that fall occurs). And the second feature value is an average value of the average reflection point information of the second predetermined number M of consecutive frames located behind in N frames, and whether fall occurs may be judged according to comparison of the average value and a threshold.

2) For the Information z on Height

Figure 6:
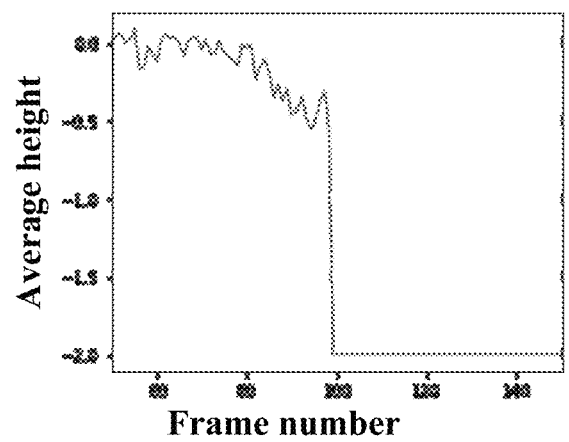
FIG. 6 is a schematic diagram of variation of reflection point height information along with time (frame number) in a fall process according to an embodiment.

FIG. 6 is a schematic diagram of variation of reflection point height information $\bar{z}$ along with time (frame number) in the fall process. As shown in FIG. 6, when the fall occurs, the average reflection point information $\bar{z}$ exhibits a downward trend, and the variation is very fast. The first feature value may be the rate of variation (slope) Stz of linear fitting between the average reflection information $\bar{z}$ and time (N frames) and/or a coefficient of correlation Rtz between the average reflection information $\bar{z}$ and time (N frames). Reference may be made to the relevant art for a method for calculating the slope of linear fitting and the coefficient of correlation. A variation tendency (gradually decreasing or increasing, or extremely quickly decreasing, etc.) of the average reflection information $\bar{z}$ may be reflected according to the slope Stz, and a magnitude of the linear correlation between the average reflection information $\bar{z}$ and time may be reflected according to the coefficient of correlation Rtz, a range of value of which being [−1, 1] (for example, the coefficient of correlation in the fall process should be of a value close to −1, in other words, if a difference between a coefficient of correlation obtained through calculation and −1 is less than or equal to a specified threshold, it is possible that fall occurs). And the second feature value is an average value of the average reflection point information of the second predetermined number M of consecutive frames located behind in N frames, and whether fall occurs may be judged according to comparison of the average value and a threshold.

3) For Information v on Radial Velocity

Figure 7:
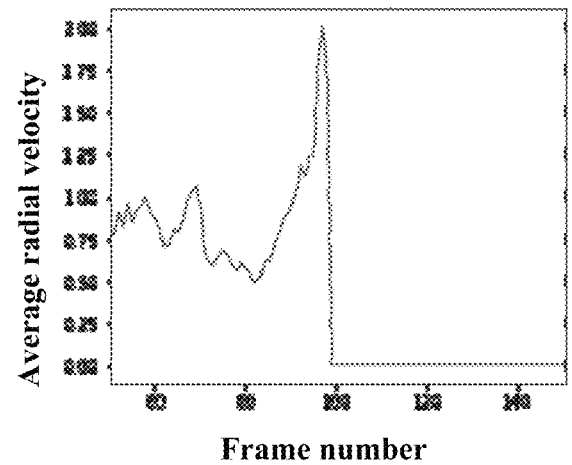
FIG. 7 is a schematic diagram of variation of reflection point radial velocity along with time (frame number) in a fall process according to an embodiment.

FIG. 7 is a schematic diagram of variation of the average reflection point information $\bar{v}$ along with time (frame number) in the fall process. As shown in FIG. 7, when the fall occurs, there exists an acceleration process, that is, the average reflection point information $\bar{v}$ exhibits rapid increase first, and then a rapid decrease trend. The first feature value may be the rate of variation (slope) Sty of linear fitting between the average reflection information $\bar{v}$ and time (N frames) and/or a coefficient of correlation Rtv between the average reflection information $\bar{v}$ and time (N frames). Reference may be made to the relevant art for a method for calculating the slope of linear fitting and the coefficient of correlation. A variation tendency (gradually decreasing or increasing, or extremely quickly decreasing, etc.) of the average reflection information $\bar{v}$ may be reflected according to the slope Sty, and a magnitude of the linear correlation between the average reflection information $\bar{z}$ and time may be reflected according to the coefficient of correlation Rtz, a range of value of which being [−1, 1] (for example, the coefficient of correlation in the fall process should be of a value close to −1, in other words, if a difference between a coefficient of correlation obtained through calculation and −1 is less than or equal to a specified threshold, it is possible that fall occurs). And the second feature value is an average value of the average reflection point information of the second predetermined number M of consecutive frames located behind in N frames, and whether fall occurs may be judged according to comparison of the average value and a threshold.

4) For the Horizontal and Vertical Coordinates (x, y) in a Horizontal Plane

Figure 8:
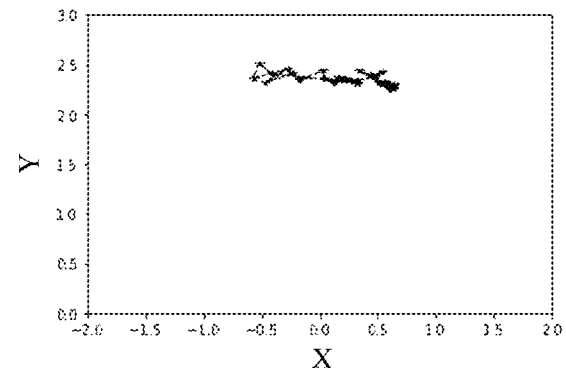
FIG. 8 is a schematic diagram of trajectory variation of variation of reflection point horizontal coordinates (x, y) along with time (frame number) in a fall process in the X-Y plane according to an embodiment.

FIG. 8 is a schematic diagram of trajectory variation of variation of the reflection point information $(\bar{x}, \bar{y})$ along with time (frame number) in a fall process in the X-Y plane. As shown in FIG. 8, when the fall occurs, the trajectory exhibits a shape similar to a straight line, that is, a direction will not significantly change in detecting fall of the detected object. A direction of the straight line is a direction in which the detected object falls. A length of the straight line reflects a change of the position of the detected object from the upright state to the lying state. The first feature value is a linear fitting error Exy between average reflection point information $\bar{x}$ of the horizontal coordinate and average reflection point information $\bar{y}$ of the vertical coordinate, a minimum value in a range of value being 0 (for example, the linear fitting error in the fall process should be of a value close to 0, the smaller the better, in other words, the smaller the linear fitting error obtained through calculation, the trajectory is closer to a shape of a straight line, that is, it is possible that fall occurs), and/or a coefficient Rxy of correlation between average reflection point information $\bar{x}$ of the horizontal coordinate and average reflection point information $\bar{y}$ of the vertical coordinate, a range of value being [−1, 1] (for example, the coefficient of correlation in the fall process should be of a value far from 0, in other words, if a difference between an absolute value of the coefficient of correlation obtained through calculation and 0 is greater than or equal to a specified threshold, or a difference between an absolute value of the coefficient of correlation obtained through calculation and 1 is lesser than or equal to a specified threshold, it is possible that fall occurs), indicating a magnitude of linear correlation between the average reflection point information $\bar{x}$ and $\bar{y}$. The second feature value is a distance between a coordinate trajectory center of a horizontal plane of the third predetermined number Q of consecutive frames located front and a coordinate trajectory center of a horizontal plane of the second predetermined number M of consecutive frames located behind. The first feature value may reflect whether the trajectory exhibits a shape of straight line, and the second feature value may reflect a length of the trajectory.

In block 403, after the first feature value and the second feature value are obtained through calculation, whether the detected object falls is determined according to the first feature value and the second feature value.

In an embodiment, the first feature value and the second feature value are compared with falling judgment threshold ranges to which the feature values correspond, and whether the detected object falls is determined according to a result of comparison. Fall training reflection point information may be pre-acquired, and the falling judgment threshold ranges are obtained by using a machine-learning algorithm. For example, results of comparison of each type of features and corresponding falling judgment threshold ranges may be integrated to obtain a final judgment result. In particular, F (greater than or equal to 2) features are compared, and if comparison results of more than L features in the F features are fall, it is judged that the final judgment result is fall. Proportions of L and F may be determined as needed, or a weighting coefficient may be set for a comparison result of each type of features, and weighted sums are respectively counted for fall and non-fall. Weighted sums of the fall and non-fall are compared, and a result of a larger value is taken as the final detection result; however, this embodiment is not limited thereto.

In an embodiment, the fall training reflection point information may be pre-acquired, and the reflection point information is scaled (fall or non-fall is a scaling tag) by using a machine-learning algorithm, so as to form a neural network for fall judgment. The first feature value and the second feature value obtained through calculation in block 403 are inputted into the trained neural network to obtain a scaling result. The machine-learning algorithm may be support vector machine (SVM) or a random forest algorithm, etc., and reference may be made to the relevant art for particulars, which shall not be described herein any further.

Figure 9:
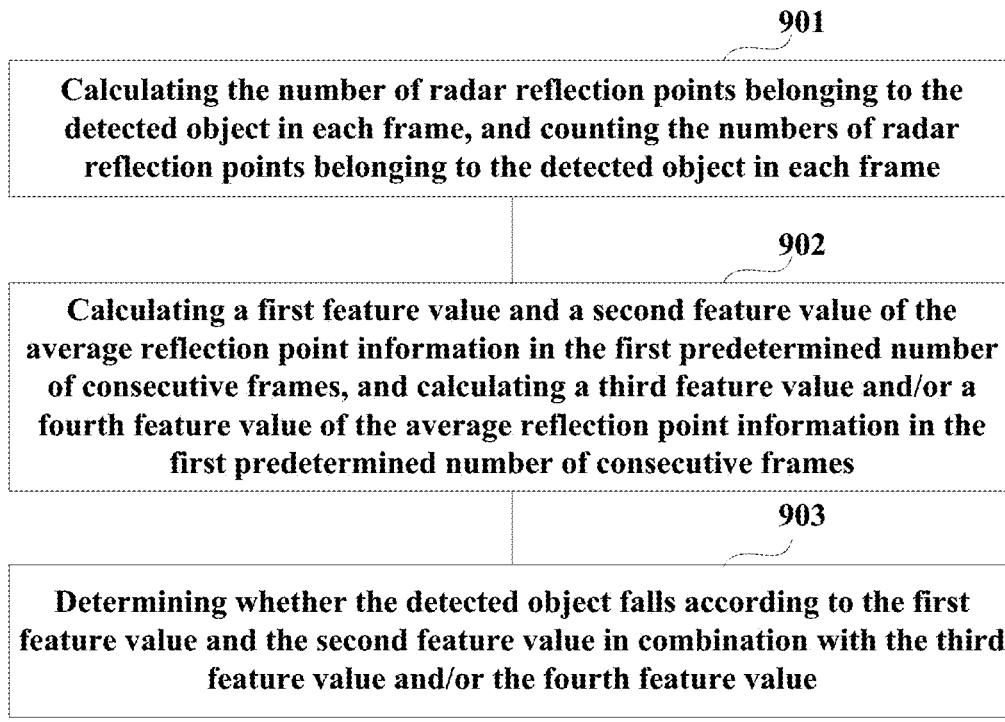
FIG. 9 is a flowchart of determining whether a detected object has fallen according to an embodiment.

FIG. 9 is a schematic diagram of another embodiment of 102. In an embodiment, the relationship of variation of the radar reflection point along with time may be denoted by using the first feature value and the second feature value, in combination with a third feature value and/or a fourth feature value. As shown in FIG. 9, the method includes:

Block 901: calculating the number of radar reflection points belonging to the detected object in each frame, and counting the numbers $n_1, n_2, \ldots n_N$, of radar reflection points belonging to the detected object in each frame;

Block 902: calculating a first feature value and a second feature value of the average reflection point information in the first predetermined number of consecutive frames, and calculating a third feature value and/or a fourth feature value of the average reflection point information in the first predetermined number of consecutive frames; and Block 903: determining whether the detected object falls according to the first feature value and the second feature value in combination with the third feature value and/or the fourth feature value.

In an embodiment, blocks 401-402 may be referred to for calculating the average reflection point information, the first feature value and the second feature value.

In an embodiment, in addition to using the reflection point information, the number of reflection points of each frame may also be used for the fall detection, which shall be described in detail below.

5) For the Number of Reflection Points

Figure 10:
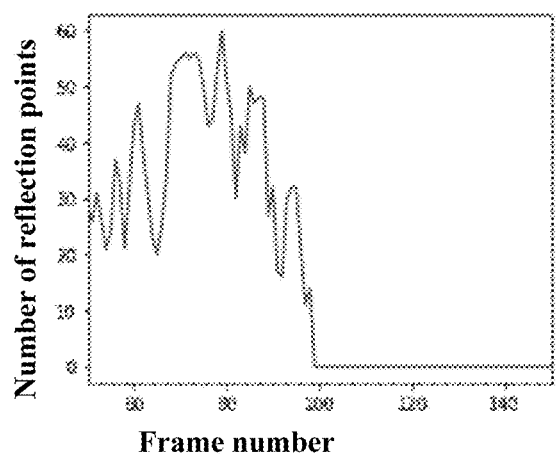
FIG. 10 is a schematic diagram of variation of the number of radar reflection points of each frame along with time (frame number) in a fall process according to an embodiment.

FIG. 10 is a schematic diagram of variation of the number of radar reflection points of each frame along with time (frame number) in the fall process. As shown in FIG. 10, when the fall occurs, due to gradual decrease of the reflection surface of the detected object, the number of radar reflection points is gradually reduced, but is not increased nor decreased extremely quickly. The third feature value is a rate of variation Stn of linear fitting between the number of radar reflection points of each frame and time, and/or a coefficient of correlation Rtn between the number of radar reflection points of each frame and time. Reference may be made to the relevant art for a method for calculating the slope of linear fitting and the coefficient of correlation. A variation tendency (gradually decreasing or increasing, or extremely quickly decreasing, etc.) of the number of reflection points may be reflected according to the slope Stn, and a magnitude of the linear correlation between the number of reflection points and time may be reflected according to the coefficient of correlation Rtn, a range of value of which being [−1, 1] (for example, the coefficient of correlation in the fall process should be of a value close to −1, in other words, if a difference between a coefficient of correlation obtained through calculation and −1 is less than or equal to a specified threshold, it is possible that fall occurs). And the fourth feature value is an average value of the number of reflection points of the second predetermined number M of consecutive frames located behind, and whether fall occurs may be judged according to comparison of the average value and a threshold.

In block 903, whether the detected object falls may be determined according to the first feature value and the second feature value in combination with the third feature value and/or the fourth feature value. For example, the fall detection is performed according to the first feature value, the second feature value and the third feature value, or the fall detection is performed according to the first feature value, the second feature value and the fourth feature value, or the fall detection is performed according to the first feature value, the second feature value, the third feature value and the fourth feature value. Reference may be made to block 403 for a particular implementation, which shall not described herein any further.

Hence, whether the detected object falls is determined according to a relationship between time and at least two of information on a position, information on a radial velocity and information on reflection signal strength in the information on reflection points obtained by the microwave radar. In the method, a terminal equipment needs not to be worn by the user, and user experience is good, which is applicable to monitoring a private area, may perform fall detection according to information on multi-dimensional reflection points, with the precision being more higher, the rate of error report being lower, and the detection speed being faster.

Embodiment 2

Figure 11:
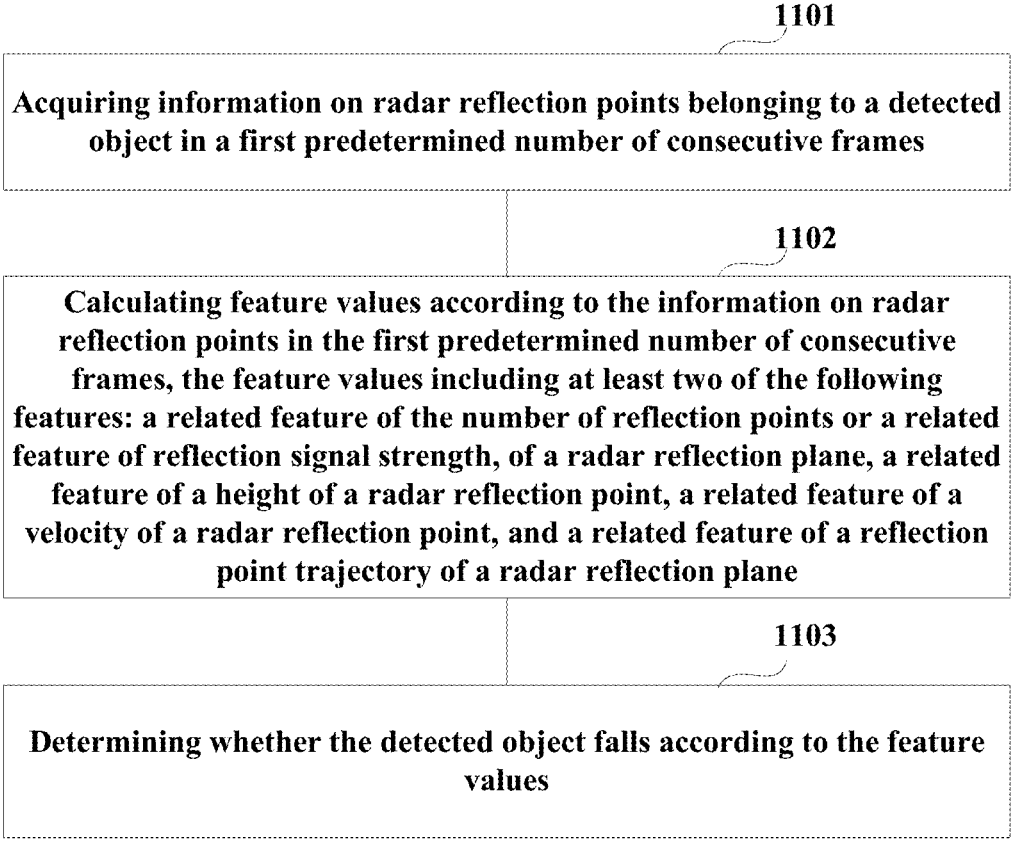
FIG. 11 is a flowchart of the fall detection method according to an embodiment.

Embodiment 2 provides a fall detection method. FIG. 11 is a flowchart of the method. As shown in FIG. 11, the method includes:

Block 1101: acquiring information on radar reflection points belonging to a detected object in a first predetermined number of consecutive frames, information on a reflection point including at least two of information on a position, information on a radial velocity and information on reflection signal strength, of the reflection point;

Block 1102: calculating feature values according to the information on radar reflection points in the first predetermined number of consecutive frames, the feature values including at least two of the following features: a feature related to the number of reflection points of a radar reflection plane or a feature related to reflection signal strength of a radar reflection plane, a feature related to a height of a radar reflection point, a feature related to a velocity of a radar reflection point, and a feature related to a reflection point trajectory of a radar reflection plane; and Block 1103: determining whether the detected object falls according to the feature values.

In an embodiment, reference may be made to block 101 in Embodiment 1 for an implementation of block 1101.

In block 1102, the feature related to the number of reflection points of a radar reflection plane includes a rate of variation (slope) of linear fitting between the number of radar reflection points of each frame and time, and/or a coefficient of correlation between the number of radar reflection points of each frame and time, and/or an average value of the numbers of radar reflection points in the second predetermined number of consecutive frames located behind. The feature related to the reflection signal strength of the radar reflection plane includes a rate of variation (slope) of linear fitting between an average reflection signal strength of radar reflection points of each frame and time, and/or a coefficient of correlation between an average reflection signal strength of radar reflection points of each frame and time, and/or an average reflection signal strength of radar reflection points in the second predetermined number of consecutive frames located behind. The feature related to a height of a radar reflection point includes a rate of variation (slope) of linear fitting between an average height of radar reflection points of each frame and time, and/or a coefficient of correlation between an average height of radar reflection points of each frame and time, and/or an average height of radar reflection points in the second predetermined number of consecutive frames located behind. The feature related to a velocity of a radar reflection point includes a rate of variation (slope) of linear fitting between an average Doppler velocity of radar reflection points of each frame and time, and/or a coefficient of correlation between an average Doppler velocity of radar reflection points of each frame and time, and/or an average Doppler velocity of radar reflection points in the second predetermined number of consecutive frames located behind. The feature related to a reflection point trajectory of a radar reflection plane includes a linear fitting error between average reflection point information of a horizontal coordinate and average reflection point information of a vertical coordinate of each frame, and/or a coefficient of correlation between average reflection point information of the horizontal coordinate and average reflection point information of the vertical coordinate of each frame, and/or a distance between a coordinate trajectory center of a horizontal plane of a third predetermined number of consecutive frames located front and a coordinate trajectory center of a horizontal plane of a second predetermined number of consecutive frames located behind.

Reference may be made to features 1)-5) in Embodiment 1 for methods for calculating the above features, and reference may be made to blocks 403 and 903 in Embodiment 1 for an implementation of block 1103, which shall not be described herein any further.

Hence, whether the detected object falls is determined according to at least two of a feature related to the number of reflection points of a radar reflection plane or a feature related to reflection signal strength of a radar reflection plane, a feature related to a height of a radar reflection point, a feature related to a velocity of a radar reflection point, and a feature related to a reflection point trajectory of a radar reflection plane. In the method, a terminal equipment needs not to be worn by the user, and user experience is good, which is applicable to monitoring a private area, may perform fall detection according to information on multi-dimensional reflection points, with the precision being more higher, the rate of error report being lower, and the detection speed being faster.

Embodiment 3

Embodiment 3 provides a fall detection apparatus. As a way of the apparatus for solving problems is similar to that of the method in Embodiment 1, reference may be made to the implementation of the method in Embodiment 1 for implementation of the apparatus, with identical contents being not going to be described herein any further.

Figure 12:
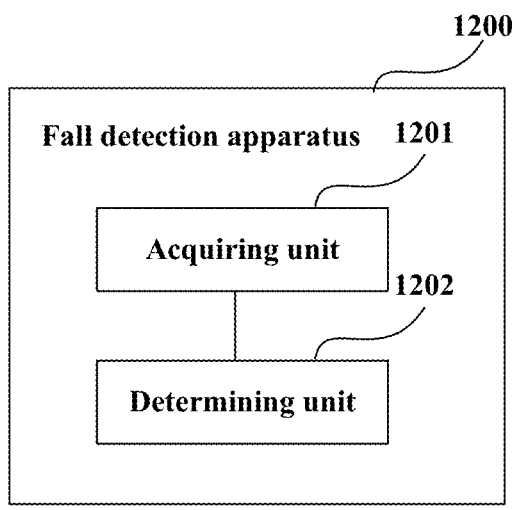
FIG. 12 is a schematic diagram of the fall detection apparatus according to an embodiment.

FIG. 12 is a schematic diagram of a structure of the fall detection apparatus. As shown in FIG. 12, the apparatus 1200 includes:

an acquiring unit 1201 configured to acquire information on radar reflection points belonging to a detected object in a first predetermined number of consecutive frames, information on a radar reflection point including at least two of information on a position, information on a radial velocity and information on reflection signal strength, of the reflection point; and a determining unit 1202 configured to determine whether the detected object falls according to a relationship between time and the information on radar reflection points in the first predetermined number of consecutive frames.

In an embodiment, reference may be made to block 101 in Embodiment 1 for an implementation of the acquiring unit 1201.

Figure 13:
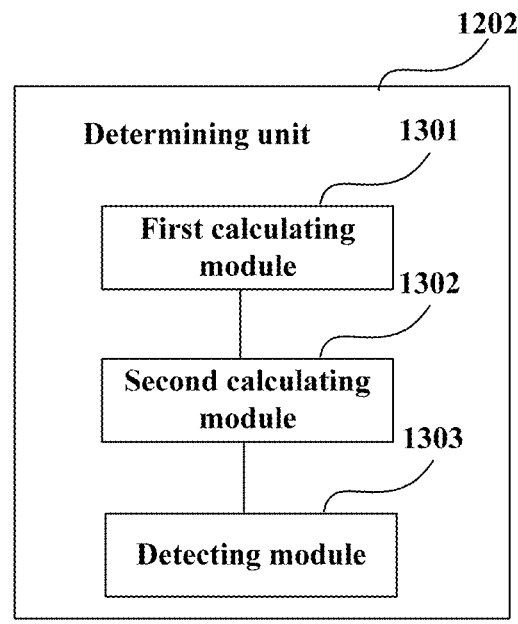
FIG. 13 is a schematic diagram of a determining unit (apparatus) according to an embodiment.

FIG. 13 is a schematic diagram of the determining unit 1202. As shown in FIG. 13, the determining unit 1202 includes:

a first calculating module 1301 configured to calculate average reflection point information of a plurality of radar reflection points belonging to the detected object in each frame;

a second calculating module 1302 configured to calculate a first feature value and a second feature value of the average reflection point information in the first predetermined number of consecutive frames, the first feature value denoting a parameter of the average reflection point information related to time variation, and the second feature value denoting a statistical value of average reflection point information of a second predetermined number of consecutive frames located behind in the first predetermined number of consecutive frames, and/or denoting a difference between a statistical value of average reflection point information of a third predetermined number of consecutive frames located front in the first predetermined number of consecutive frames and a statistical value of average reflection point information of a second predetermined number of consecutive frames located behind in the first predetermined number of consecutive frames; and a detecting module 1303 configured to determine whether the detected object falls according to the first feature value and the second feature value.

In an embodiment, the apparatus 1200 further includes:

a third calculating module (not shown, optional) configured to count the number of radar reflection points belonging to the detected object in each frame, and calculate a third feature value and/or a fourth feature value of the number of radar reflection points, the third feature value denoting a parameter of the number of radar reflection points related to time variation, and the fourth feature value denoting an average value of the number of radar reflection points of the second predetermined number of consecutive frames located behind;

and the detecting module 1303 determines whether the detected object falls according to the first feature value, the second feature value, the third feature value and/or the fourth feature value.

In an embodiment, reference may be made to Embodiment 1 for meanings of the first feature value, the second feature value, the third feature value and the fourth feature value, reference may be made to blocks 401-403 in Embodiment 1 for implementations of the first calculating module 1301, the second calculating module 1302 and the detecting module 1303, and reference may be made to block 902 in Embodiment 1 for an implementation of the third calculating module.

In an embodiment, the apparatus 1200 further includes:

a training unit (not shown, optional) configured to acquire information on reflection points of falling training, and obtain a range of the falling judgment thresholds by using a machine learning algorithm.

Hence, whether the detected object falls is determined according to a relationship between time and at least two of information on a position, information on a radial velocity and information on reflection signal strength in the information on reflection points obtained by the microwave radar. In the method, a terminal equipment needs not to be worn by the user, and user experience is good, which is applicable to monitoring a private area, may perform fall detection according to information on multi-dimensional reflection points, with the precision being more higher, the rate of error report being lower, and the detection speed being faster.

Embodiment 4

Embodiment 4 provides a fall detection apparatus. As a way of the apparatus for solving problems is similar to that of the method in Embodiment 2, reference may be made to the implementation of the method in Embodiment 2 for implementation of the apparatus, with identical contents being not going to be described herein any further.

Figure 14:
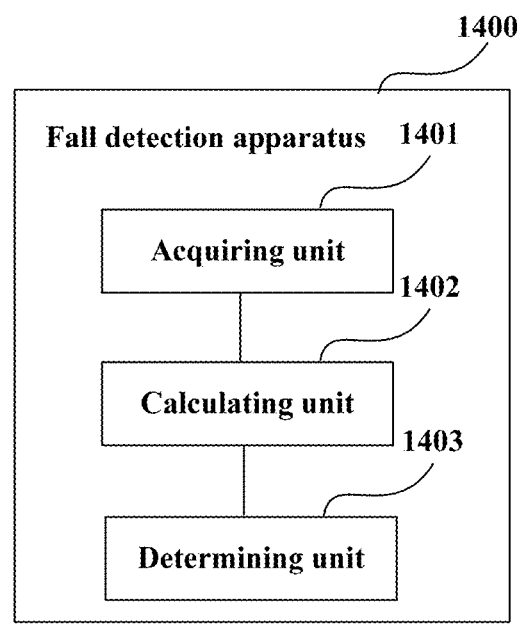
FIG. 14 is a schematic diagram of the fall detection apparatus according to an embodiment.

FIG. 14 is a schematic diagram of a structure of the fall detection apparatus. As shown in FIG. 14, the apparatus 1400 includes:

an acquiring unit 1401 configured to acquire information on radar reflection points belonging to a detected object in a first predetermined number of consecutive frames, information on a reflection point including at least two of information on a position, information on a radial velocity and information on reflection signal strength, of the reflection point;

a calculating unit 1402 configured to calculate feature values according to the information on radar reflection points in the first predetermined number of consecutive frames, the feature values including at least two of the following features: a feature related to the number of reflection points of a radar reflection plane or a feature related to reflection signal strength of a radar reflection plane, a feature related to a height of a radar reflection point, a feature related to a velocity of a radar reflection point, and a feature related to a reflection point trajectory of a radar reflection plane; and a determining unit 1403 configured to determine whether the detected object falls according to the feature values.

In an embodiment, reference may be made to features 1)-5) in Embodiment 1 for methods for calculating the feature related to the number of reflection points, or the feature related to reflection signal strength, of the radar reflection plane, the feature related to the height of radar reflection points, the feature related to the velocity of the radar reflection points, and the feature related to the reflection point trajectory of the radar reflection plane, which shall not be described herein any further.

In an embodiment, reference may be made to Embodiment 2 for implementations of the acquiring unit 1401, the calculating unit 1402 and the determining unit 1403, which shall not be described herein any further.

Hence, whether the detected object falls is determined according to at least two of a feature related to the number of reflection points of a radar reflection plane or a feature related to reflection signal strength of a radar reflection plane, a feature related to a height of a radar reflection point, a feature related to a velocity of a radar reflection point, and a feature related to a reflection point trajectory of a radar reflection plane. In the method, a terminal equipment needs not to be worn by the user, and user experience is good, which is applicable to monitoring a private area, may perform fall detection according to information on multi-dimensional reflection points, with the precision being more higher, the rate of error report being lower, and the detection speed being faster.

Embodiment 5

This embodiment provides a fall detection system, including an electronic device and a microwave radar. The electronic device may be, for example, a computer, a server, a work station, a lap-top computer, and a smart mobile phone, etc.; however, this embodiment is not limited thereto. Reference may be made to Embodiment 1 for a structure of the microwave radar, which is used to transmit microwave signals, receive reflected signals, and calculate information on all reflection points based on the transmitted microwave signals and the reflected signals (the function of calculating information on all reflection points may also be executed by the electronic device). The electronic device acquires information on radar reflection points belonging to a detected object, and determines whether the detected object falls according to a relationship between time and the information on radar reflection points in the first predetermined number of consecutive frames; or the electronic device acquires information on radar reflection points belonging to a detected object, calculates feature values according to the information on radar reflection points in the first predetermined number of consecutive frames, the feature values including at least two of the following features: a feature related to the number of reflection points of a radar reflection plane or a feature related to reflection signal strength of a radar reflection plane, a feature related to a height of a radar reflection point, a feature related to a velocity of a radar reflection point, and a feature related to a reflection point trajectory of a radar reflection plane, and determines whether the detected object falls according to the feature values.

Figure 15:
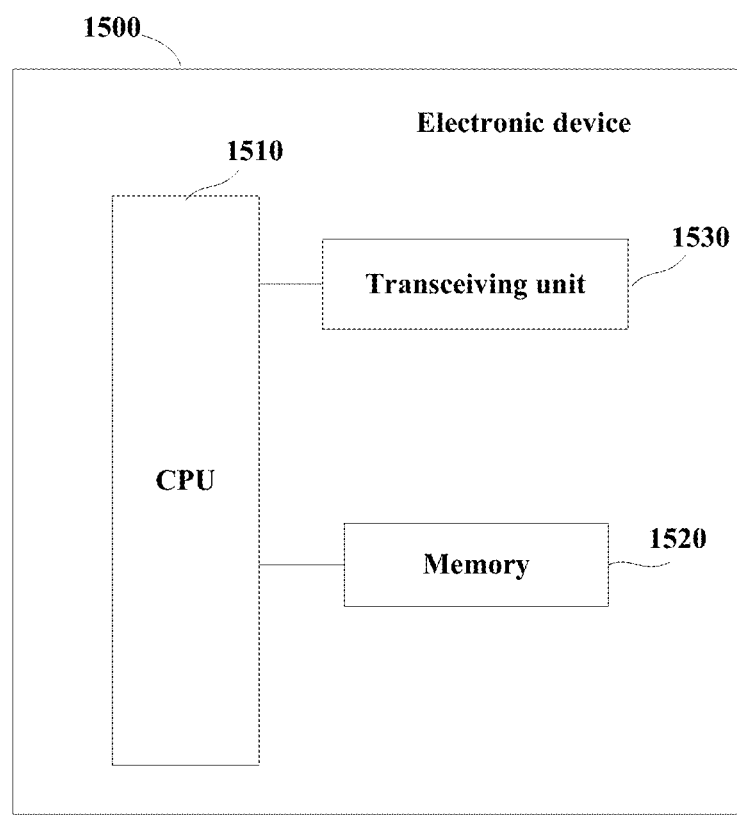
FIG. 15 is a schematic diagram of the electronic device according to an embodiment.

FIG. 15 is a schematic diagram of the electronic device of the embodiment of this disclosure. As shown in FIG. 15, the electronic device 1500 may include a processor 1510 (such as a central processing unit (CPU)) and a memory 1520, the memory 1520 being coupled to the processor 1510. The memory 1520 may store various data, and furthermore, it may store a program 1521 for data processing, and execute the program 1521 under control of the processor 1510.

In one embodiment, the functions of the fall detection apparatus 1200 or the fall detection apparatus 1400 may be integrated into the processor 1510, the processor 1510 may be configured to carry out the fall detection method described in Embodiment 1 or the fall detection method described in Embodiment 2.

In another embodiment, the fall detection apparatus 1200 or the fall detection apparatus 1400 and the processor 1510 may be configured separately; for example, the fall detection apparatus 1200 or the fall detection apparatus 1400 may be configured as a chip connected to the processor 1510, and the functions of the fall detection apparatus 1200 or the fall detection apparatus 1400 are executed under control of the processor 1510.

For example, the processor 1510 may be configured to executed the following control: acquiring information on radar reflection points belonging to a detected object in a first predetermined number of consecutive frames, and determining whether the detected object falls according to a relationship between time and the information on radar reflection points in the first predetermined number of consecutive frames;

or acquiring information on radar reflection points belonging to a detected object in a first predetermined number of consecutive frames, calculating feature values according to the information on radar reflection points in the first predetermined number of consecutive frames, the feature values including at least two of the following features: a feature related to the number of reflection points of a radar reflection plane or a feature related to reflection signal strength of a radar reflection plane, a feature related to a height of a radar reflection point, a feature related to a velocity of a radar reflection point, and a feature related to a reflection point trajectory of a radar reflection plane, and determining whether the detected object falls according to the feature values.

Reference may be made to Embodiment 1 or 2 for a particular implementation of the processor 1510, which shall not be described herein any further.

Furthermore, as shown in FIG. 15, the electronic device 1500 may include a transceiving unit 1530, etc.; functions of the above components are similar to those in the relevant art, which shall not be described herein any further. It should be noted that the electronic device 1500 does not necessarily include all the parts shown in FIG. 15, and furthermore, the electronic device 1500 may include parts not shown in FIG. 15, and the relevant art may be referred to.

An embodiment of the present disclosure provides a computer readable program code, which, when executed in a fall detection apparatus, will cause a computer to carry out the fall detection method as described in Embodiment 1 in the fall detection apparatus.

An embodiment of the present disclosure provides a computer readable medium, including a computer readable program code, which will cause a computer to carry out the fall detection method as described in Embodiment 1 in a fall detection apparatus.

An embodiment of the present disclosure provides a computer readable program code, which, when executed in a fall detection apparatus, will cause a computer to carry out the fall detection method as described in Embodiment 2 in the fall detection apparatus.

An embodiment of the present disclosure provides a computer readable medium, including a computer readable program code, which will cause a computer to carry out the fall detection method as described in Embodiment 2 in a fall detection apparatus.

The method in an apparatus described with reference to the embodiments of this disclosure may be directly embodied as hardware, software modules executed by a processor, or a combination thereof. For example, one or more functional block diagrams and/or one or more combinations of the functional block diagrams shown in FIGS. 12-15 may either correspond to software modules of procedures of a computer program, or correspond to hardware modules. Such software modules may respectively correspond to the blocks shown in FIGS. 1, 4, 9 and 11. And the hardware module, for example, may be carried out by firming the soft modules by using a field programmable gate array (FPGA).

The soft modules may be located in an RAM, a flash memory, an ROM, an EPROM, and EEPROM, a register, a hard disc, a floppy disc, a CD-ROM, or any memory medium in other forms known in the art. A memory medium may be coupled to a processor, so that the processor may be able to read information from the memory medium, and write information into the memory medium; or the memory medium may be a component of the processor. The processor and the memory medium may be located in an ASIC. The soft modules may be stored in a memory of an apparatus, and may also be stored in a memory card of a pluggable apparatus.

One or more functional blocks and/or one or more combinations of the functional blocks in FIGS. 12-15 may be realized as a universal processor, a digital signal processor (DSP), an application-specific integrated circuit (ASIC), a field programmable gate array (FPGA) or other programmable logic devices, discrete gate or transistor logic devices, discrete hardware component or any appropriate combinations thereof carrying out the functions described in this application. And the one or more functional block diagrams and/or one or more combinations of the functional block diagrams in FIGS. 12-15 may also be realized as a combination of computing equipment, such as a combination of a DSP and a microprocessor, multiple processors, one or more microprocessors in communication combination with a DSP, or any other such configuration.

This disclosure is described above with reference to particular embodiments. However, it should be understood by those skilled in the art that such a description is illustrative only, and not intended to limit the protection scope of the present invention. Various variants and modifications may be made by those skilled in the art according to the spirits and principle of the present invention, and such variants and modifications fall within the scope of the present invention.

For implementations of this disclosure containing the above embodiments, following supplements are further disclosed.

Supplement 1. A fall detection apparatus, including:

an acquiring unit configured to acquire information on radar reflection points belonging to a detected object in a first predetermined number of consecutive frames, information on a reflection point including at least two of information on a position, information on a radial velocity and information on reflection signal strength, of the reflection point; and a determining unit configured to determine whether the detected object falls according to a relationship between time and the information on radar reflection points in the first predetermined number of consecutive frames.

Supplement 2. The apparatus according to supplement 1, wherein the information on the position of the reflection point includes at least one of information on a distance between the reflection point and a radar and information on a three-dimensional coordinate of the reflection point.

Supplement 3. The apparatus according to supplement 1, wherein the determining unit includes:

a first calculating module configured to calculate average reflection point information of a plurality of radar reflection points belonging to the detected object in each frame;

a second calculating module configured to calculate a first feature value and a second feature value of the average reflection point information in the first predetermined number of consecutive frames, the first feature value denoting a parameter of the average reflection point information related to time variation, and the second feature value denoting a statistical value of average reflection point information of a second predetermined number of consecutive frames located behind in the first predetermined number of consecutive frames, and/or denoting a difference between a statistical value of average reflection point information of a third predetermined number of consecutive frames located front in the first predetermined number of consecutive frames and a statistical value of average reflection point information of a second predetermined number of consecutive frames located behind in the first predetermined number of consecutive frames; and a detecting module configured to determine whether the detected object falls according to the first feature value and the second feature value.

Supplement 4. The apparatus according to supplement 3, wherein when the information on the reflection point is information on a height in the information on three-dimensional coordinate of the reflection point, or the information on the reflection signal strength, or the information on the radial velocity, the first feature value is a rate of variation of linear fitting between average reflection point information and time, and/or a coefficient of correlation between the average reflection point information and time, and the second feature value is an average value of the average reflection point information of the second predetermined number of consecutive frames located behind.

Supplement 5. The apparatus according to supplement 3, wherein when the information on the reflection point is information on horizontal and vertical coordinates of a horizontal plane in the information on three-dimensional coordinate of the reflection point, the first feature value is a linear fitting error between average reflection point information of the horizontal coordinate and average reflection point information of the vertical coordinate, and/or a coefficient of correlation between average reflection point information of the horizontal coordinate and average reflection point information of the vertical coordinate, and the second feature value is a distance between a coordinate trajectory center of a horizontal plane of the third predetermined number of consecutive frames located front and a coordinate trajectory center of a horizontal plane of the second predetermined number of consecutive frames located behind.

Supplement 6. The apparatus according to supplement 3, wherein the apparatus further includes:

a third calculating module configured to count the number of radar reflection points belonging to the detected object in each frame, and calculate a third feature value and/or a fourth feature value of the number of radar reflection points, the third feature value denoting a parameter of the number of reflection points related to time variation, and the fourth feature value denoting an average value of the number of reflection points of the second predetermined number of consecutive frames located behind;

and the detecting module determines whether the detected object falls according to the first feature value, the second feature value, the third feature value and/or the fourth feature value.

Supplement 7. The apparatus according to supplement 6, wherein the third feature value is a rate of variation of linear fitting between the number of radar reflection points of each frame and time, and/or a coefficient of correlation between the number of radar reflection points of each frame and time.

Supplement 8. The apparatus according to supplement 3 or 6, wherein the detecting module compares the first feature value and the second feature value, or the first feature value, the second feature value, the third feature value and/or the fourth feature value, with falling judgment thresholds to which the feature values correspond, and determines whether the detected object falls according to a result of comparison.

Supplement 9. The apparatus according to supplement 8, wherein the apparatus further includes:

a training unit configured to acquire information on reflection points of falling training, and obtain a range of the falling judgment thresholds by using a machine learning algorithm.

Supplement 10. A fall detection apparatus, including:

an acquiring unit configured to acquire information on radar reflection points belonging to a detected object in a first predetermined number of consecutive frames, information on a reflection point comprising at least two of information on a position, information on a radial velocity and information on reflection signal strength, of the reflection point;

a calculating unit configured to calculate feature values according to the information on radar reflection points in the first predetermined number of consecutive frames, the feature values comprising at least two of the following features: a feature related to the number of reflection points of a radar reflection plane, or a feature related to reflection signal strength of a radar reflection plane, a feature related to a height of a radar reflection point, a feature related to a velocity of a radar reflection point, and a feature related to a reflection point trajectory of a radar reflection plane; and a determining unit configured to determine whether the detected object falls according to the feature values.

Supplement 11. The apparatus according to supplement 10, wherein the feature related to the number of reflection points of a radar reflection plane includes a rate of variation (slope) of linear fitting between the number of radar reflection points of each frame and time, and/or a coefficient of correlation between the number of radar reflection points of each frame and time, and/or an average value of the numbers of radar reflection points in the second predetermined number of consecutive frames located behind.

Supplement 12. The apparatus according to supplement 10, wherein the feature related to the reflection signal strength of the radar reflection plane includes a rate of variation (slope) of linear fitting between an average reflection signal strength of radar reflection points of each frame and time, and/or a coefficient of correlation between an average reflection signal strength of radar reflection points of each frame and time, and/or an average reflection signal strength of radar reflection points in the second predetermined number of consecutive frames located behind.

Supplement 13. The apparatus according to supplement 10, wherein the feature related to a height of a radar reflection point includes a rate of variation (slope) of linear fitting between an average height of radar reflection points of each frame and time, and/or a coefficient of correlation between an average height of radar reflection points of each frame and time, and/or an average height of radar reflection points in the second predetermined number of consecutive frames located behind.

Supplement 14. The apparatus according to supplement 10, wherein the feature related to a velocity of a radar reflection point includes a rate of variation (slope) of linear fitting between an average Doppler velocity of radar reflection points of each frame and time, and/or a coefficient of correlation between an average Doppler velocity of radar reflection points of each frame and time, and/or an average Doppler velocity of radar reflection points in the second predetermined number of consecutive frames located behind.

Supplement 15. The apparatus according to supplement 10, wherein the feature related to a reflection point trajectory of a radar reflection plane includes a linear fitting error between average reflection point information of a horizontal coordinate and average reflection point information of a vertical coordinate of each frame, and/or a coefficient of correlation between average reflection point information of the horizontal coordinate and average reflection point information of the vertical coordinate of each frame, and/or a distance between a coordinate trajectory center of a horizontal plane of a third predetermined number of consecutive frames located front and a coordinate trajectory center of a horizontal plane of a second predetermined number of consecutive frames located behind.

Supplement 16. A fall detection method, including:
acquiring information on radar reflection points belonging to a detected object in a first predetermined number of consecutive frames, information on a reflection point including at least two of information on a position, information on a radial velocity and information on reflection signal strength, of the reflection point; and
determining whether the detected object falls according to a relationship between time and the information on radar reflection points in the first predetermined number of consecutive frames.

Supplement 17. The method according to supplement 16, wherein the determining whether the detected object falls according to a relationship between time and the information on radar reflection points in the first predetermined number of consecutive frames comprises:

calculating average reflection point information of a plurality of radar reflection points belonging to the detected object in each frame;
calculating a first feature value and a second feature value of the average reflection point information in the first predetermined number of consecutive frames, the first feature value denoting a parameter of the average reflection point information related to time variation, and the second feature value denoting a statistical value of average reflection point information of a second predetermined number of consecutive frames located behind in the first predetermined number of consecutive frames, and/or denoting a difference between a statistical value of average reflection point information of a third predetermined number of consecutive frames located front in the first predetermined number of consecutive frames and a statistical value of average reflection point information of a second predetermined number of consecutive frames located behind in the first predetermined number of consecutive frames; and
determining whether the detected object falls according to the first feature value and the second feature value.

Supplement 18. The method according to supplement 17, wherein when the information on the reflection point is information on a height in the information on three-dimensional coordinate of the reflection point, or the information on reflection signal strength, or the information on the radial velocity, the first feature value is a rate of variation of linear fitting between the average reflection information and time, and/or a coefficient of correlation between the average reflection information and time, and the second feature value is an average value of the average reflection point information of the second predetermined number of consecutive frames located behind.

Supplement 19. The method according to supplement 17, wherein when the information on the reflection point is information on horizontal and vertical coordinates of a horizontal plane in the information on a three-dimensional coordinate of the reflection point, the first feature value is a linear fitting error between average reflection point information of the horizontal coordinate and average reflection point information of the vertical coordinate, and/or a coefficient of correlation between average reflection point information of the horizontal coordinate and average reflection point information of the vertical coordinate, and the second feature value is a distance between a coordinate trajectory center of a horizontal plane of the third predetermined number of consecutive frames located front and a coordinate trajectory center of a horizontal plane of the second predetermined number of consecutive frames located behind.

Supplement 20. The method according to supplement 17, wherein the method further includes:
counting the number of radar reflection points belonging to the detected object in each frame, and calculate a third feature value and/or a fourth feature value of the number of radar reflection points, the third feature value denoting a parameter of the number of radar reflection points related to time variation, and the fourth feature value denoting an average value of the number of radar reflection points of the second predetermined number of consecutive frames located behind;
and whether the detected object falls is determined according to the first feature value, the second feature value, the third feature value and/or the fourth feature value.

What is claimed is:
1. A fall detection apparatus, comprising:
a memory;

a processor coupled to the memory and the processor configured to:
  acquire information of radar detection points belonging to a detected object in a predetermined number of consecutive frames, information of a radar detection point among the radar detection points including at least two of information on a position, information on a radial velocity and information on reflection signal strength; and
  determine whether the detected object has fallen according to a relationship between time and the information of the radar detection points in the predetermined number of consecutive frames;
wherein the predetermined number of consecutive frames are a first predetermined number of consecutive frames and the processor is further configured to:
calculate average detection point information of a plurality of radar detection points belonging to the detected object in each frame, wherein the average detection point information is an average value of each of the information of the plurality of radar detection points;
calculate a first feature value and a second feature value of the average detection point information in the first predetermined number of consecutive frames,
where the first feature value denotes:
  a parameter of the average detection point information related to time variation, and the second feature value denoting a statistical value of average detection point information of a second predetermined number of consecutive frames located behind the first predetermined number of consecutive frames, and/or
  a difference between a statistical value of average detection point information of a third predetermined number of consecutive frames located in front of the first predetermined number of consecutive frames and a statistical value of average detection point information of the second predetermined number of consecutive frames located behind the first predetermined number of consecutive frames; and
determine whether the detected object has fallen according to the first feature value and the second feature value.

2. The fall detection apparatus according to claim 1, wherein the information on the position of the radar detection point includes at least one of information on a distance between the radar detection point and a radar and information on a three-dimensional coordinate of the radar detection point.

3. The fall detection apparatus according to claim 1, wherein when the information of the radar detection point is information of a height in information on a three-dimensional coordinate of the radar detection point, or the information on the reflection signal strength, or the information on the radial velocity, the first feature value is a rate of variation of linear fitting between average detection point information and time, and/or a coefficient of correlation between the average detection point information and time, and the second feature value is an average value of the average detection point information of the second predetermined number of consecutive frames located behind the first predetermined number of consecutive frames.

4. The fall detection apparatus according to claim 1, wherein when the information of the radar detection point is respective information of a horizontal coordinate and a vertical coordinate of a horizontal plane in information on a three-dimensional coordinate of the radar detection point, the first feature value is a linear fitting error between average detection point information of the horizontal coordinate and average detection point information of the vertical coordinate, and/or a coefficient of correlation between average detection point information of the horizontal coordinate and average detection point information of the vertical coordinate, and
the second feature value is a distance between a coordinate trajectory center of a horizontal plane of the third predetermined number of consecutive frames located in front of the first predetermined number of consecutive frames and a coordinate trajectory center of a horizontal plane of the second predetermined number of consecutive frames located behind the first predetermined number of consecutive frames.

5. The fall detection apparatus according to claim 1, wherein the processor is further configured to:
  count a number of radar detection points belonging to the detected object in each frame, and
  calculate a third feature value and/or a fourth feature value of the number of radar detection points,
  where the third feature value denotes a parameter of the number of detection points related to time variation, and the fourth feature value denotes an average value of the number of detection points of the second predetermined number of consecutive frames located behind the first predetermined number of consecutive frames; and
  determine whether the detected object has fallen according to the first feature value, the second feature value, the third feature value and/or the fourth feature value.

6. The fall detection apparatus according to claim 5, wherein the third feature value is a rate of variation of linear fitting between the number of radar detection points of each frame and time, and/or a coefficient of correlation between the number of radar detection points of each frame and time.

7. The fall detection apparatus according to claim 1, wherein the processor compares the first feature value and the second feature value, or the first feature value, the second feature value, the third feature value and/or the fourth feature value, with respective falling judgment thresholds, and determines whether the detected object has fallen according to a result of comparison.

8. The fall detection apparatus according to claim 7, wherein the processor is further configured to:
  acquire information on detection points of falling training, and obtain a range of the falling judgment thresholds by using a machine learning algorithm.

9. A fall detection apparatus, comprising:
a memory;
a processor coupled to the memory and the processor configured to:
  acquire information on radar detection points belonging to a detected object in a predetermined number of consecutive frames, information of a radar detection point among the radar detection points including at least two of information on a position, information on a radial velocity and information on reflection signal strength;
  calculate feature values according to the information on radar detection points in the predetermined number of consecutive frames, the feature values including at least two of a feature related to a number of detection points of a radar reflection plane, or a feature related to reflection signal strength of a radar reflection plane, a feature related to a height of a radar detection point, a feature related to a velocity of a radar detection point, and a feature related to a detection point trajectory of a radar reflection plane; and determine whether the detected object has fallen according to the feature values;

wherein the predetermined number of consecutive frames are a first predetermined number of consecutive frames, and the feature related to the number of detection points of a radar reflection plane includes a rate of variation (slope) of linear fitting between the number of radar detection points of each frame and time, and a coefficient of correlation between the number of radar detection points of each frame and time, and an average value of the numbers of radar detection points in a second predetermined number of consecutive frames located behind the first predetermined number of consecutive frames, the feature related to the reflection signal strength of the radar reflection plane includes a rate of variation (slope) of linear fitting between an average reflection signal strength of radar detection points of each frame and time, and a coefficient of correlation between an average reflection signal strength of radar detection points of each frame and time, and an average reflection signal strength of radar detection points in the second predetermined number of consecutive frames located behind the first predetermined number of consecutive frames, the feature related to a height of a radar detection point includes a rate of variation (slope) of linear fitting between an average height of radar detection points of each frame and time, and a coefficient of correlation between an average height of radar detection points of each frame and time, and an average height of radar detection points in the second predetermined number of consecutive frames located behind the first predetermined number of consecutive frames, the feature related to a velocity of a radar detection point includes a rate of variation (slope) of linear fitting between an average Doppler velocity of radar detection points of each frame and time, and a coefficient of correlation between an average Doppler velocity of radar detection points of each frame and time, and an average Doppler velocity of radar detection points in the second predetermined number of consecutive frames located behind the first predetermined number of consecutive frames, the feature related to a detection point trajectory of a radar reflection plane includes a linear fitting error between average detection point information of a horizontal coordinate and average detection point information of a vertical coordinate of each frame, and a coefficient of correlation between average detection point information of the horizontal coordinate and average detection point information of the vertical coordinate of each frame, and a distance between a coordinate trajectory center of a horizontal plane of a third predetermined number of consecutive frames located in front of the first predetermined number of consecutive frames and a coordinate trajectory center of a horizontal plane of a second predetermined number of consecutive frames located behind the first predetermined number of consecutive frames.

10. A fall detection method, comprising:

acquiring information of radar detection points belonging to a detected object in a predetermined number of consecutive frames, information on a radar detection point among the radar detection points including at least two of information on a position, information on a radial velocity and information on reflection signal strength; and determining whether the detected object has fallen according to a relationship between time and the information of radar detection points in the predetermined number of consecutive frames, wherein the predetermined number of consecutive frames are a first predetermined number of consecutive frames and the determining of whether the detected object has fallen according to a relationship between time and the information of radar detection points in the predetermined number of consecutive frames includes:

calculating average detection point information of a plurality of radar detection points belonging to the detected object in each frame, wherein the average detection point information is an average value of each the information of the plurality of radar detection points;

calculating a first feature value and a second feature value of the average detection point information in the first predetermined number of consecutive frames, where the first feature value denotes:

a parameter of the average detection point information related to time variation, and the second feature value denoting a statistical value of average detection point information of a second predetermined number of consecutive frames located behind the first predetermined number of consecutive frames, and/or a difference between a statistical value of average detection point information of a third predetermined number of consecutive frames located in front of the first predetermined number of consecutive frames and a statistical value of average detection point information of the second predetermined number of consecutive frames located behind the first predetermined number of consecutive frames; and determining whether the detected object has fallen according to the first feature value and the second feature value.

11. The fall detection method according to claim 10, wherein when the information of the radar detection point is information of a height in information on a three-dimensional coordinate of the radar detection point, or the information on reflection signal strength, or the information on the radial velocity, the first feature value is a rate of variation of linear fitting between the average reflection information and time, and/or a coefficient of correlation between the average reflection information and time, and the second feature value is an average value of the average detection point information of the second predetermined number of consecutive frames located behind the first predetermined number of consecutive frames.

12. The fall detection method according to claim 10, wherein when the information of the radar detection point is information on a horizontal coordinate and a vertical coordinate of a horizontal plane in information on a three-dimensional coordinate of the detection point, the first feature value is a linear fitting error between average detection point information of the horizontal coordinate and average detection point information of the vertical coordinate, and/or a coefficient of correlation between average detection point information of the horizontal coordinate and average detection point information of the vertical coordinate, and the second feature value is a distance between a coordinate trajectory center of a horizontal plane of the third predetermined number of consecutive frames located in front of the first predetermined number of consecutive frames and a coordinate trajectory center of a horizontal plane of the second predetermined number of consecutive frames located behind the first predetermined number of consecutive frames.

13. The fall detection method according to claim 10, wherein the method further includes:

counting a number of radar detection points belonging to the detected object in each frame, and calculate a third feature value and/or a fourth feature value of the number of radar detection points, where the third feature value denotes a parameter of the number of radar detection points related to time variation, and the fourth feature value denotes an average value of the number of radar detection points of the second predetermined number of consecutive frames located behind the first predetermined number of consecutive frames; and whether the detected object falls is determined according to the first feature value, the second feature value, the third feature value and/or the fourth feature value.

* * * * *